United States Patent [19]

Andersson

[11] 4,363,322
[45] Dec. 14, 1982

[54] DEODORIZING AND DISINFECTING LIQUID-ABSORBING PRODUCT AND PROCESS FOR PRODUCTION THEREOF

[76] Inventor: Bror A. E. Andersson, Österängsvägen 24, S-180 10 Enebyberg, Sweden

[21] Appl. No.: 29,433

[22] Filed: Apr. 12, 1979

[30] Foreign Application Priority Data

Apr. 13, 1978 [SE] Sweden .............................. 7804195
Aug. 28, 1978 [SE] Sweden .............................. 7809038

[51] Int. Cl.³ .................................................. A61F 13/16
[52] U.S. Cl. ................................................... 128/290 R
[58] Field of Search ................................ 128/155–156, 128/284–287, 290, 296; 423/415 R, 415 P, 385, 387, 579; 252/186; 8/101, 111, 137

[56] References Cited

U.S. PATENT DOCUMENTS

| | | | |
|---|---|---|---|
| 903,895 | 11/1908 | Schulz | 128/290 R |
| 1,702,530 | 2/1929 | Williams | 128/290 R |
| 1,950,286 | 3/1934 | Barkow | 128/290 R |
| 1,950,957 | 3/1934 | Wilhelm | 128/290 R |
| 3,073,309 | 1/1963 | Mosier | 128/290 R |
| 3,407,814 | 10/1968 | George et al. | 128/290 R |
| 3,490,454 | 1/1970 | Goldfarb et al. | 128/290 R |
| 3,570,492 | 3/1971 | Bettencourt | 128/290 R |
| 3,691,271 | 9/1972 | Charle et al. | 128/290 R |
| 3,804,094 | 4/1974 | Manoussos et al. | 128/290 R |
| 3,954,107 | 5/1976 | Chesky et al. | 128/290 R |
| 4,130,392 | 12/1978 | Diehl et al. | 8/111 |
| 4,170,453 | 10/1979 | Kitko | 8/111 |

FOREIGN PATENT DOCUMENTS

| | | |
|---|---|---|
| 50081 | 3/1935 | Denmark . |
| 79755 | 2/1895 | Fed. Rep. of Germany . |
| 244329 | 3/1912 | Fed. Rep. of Germany . |
| 487402 | 12/1929 | Fed. Rep. of Germany ... 128/290 R |
| 577798 | 6/1933 | Fed. Rep. of Germany . |
| 2305998 | 2/1973 | Fed. Rep. of Germany . |
| 2635508 | 2/1977 | Fed. Rep. of Germany . |

Primary Examiner—C. Fred Rosenbaum
Attorney, Agent, or Firm—Young & Thompson

[57] ABSTRACT

Deodorizing and disinfecting liquid-absorbing product, such as a sanitary napkin, a compress or a diaper, comprising a liquid absorbing material and inside the product at a distance from its outer edges a substance, which gives off oxygen in contact with moisture. A liquid-absorbing product into which can be inserted an insert such as a deodorizing strip or powder which gives off oxygen when in contact with moisture, which product is divided into essentially identical essentially rectangular or square pad-formed parts joined together by a thin flexible joint in such a manner that the parts can be placed on top of one another by folding the joint and then forming the product in the form in which it is to be used. A process for production of the two-part liquid-absorbing product by forming two thin, essentially square or rectangular pads, laying the pads side by side with two sides parallel and with a gap between them on a web of jacket material with the gap parallel to the longitudinal direction of the web, the width of the web being somewhat larger than the circumference around the pads laying side by side, folding the web lengthwise around the outer edges of the pads and joining the edges of the web on top of one pad so that the pads will lie enclosed by a sleeve, cutting off the web on either side of the pads, joining the two layers of jacket material in the gap between pads by glueing or fusing and either forming a seam in the jacket ends outside the pads in the plane of the pads or folding the product along the gap and laying the pads on top of each other and then forming a flat seam in the four layers of jacket material outside the pads along the intermediate surface between the pads or tying the jacket layers in a knot on each side of the pads.

10 Claims, 12 Drawing Figures

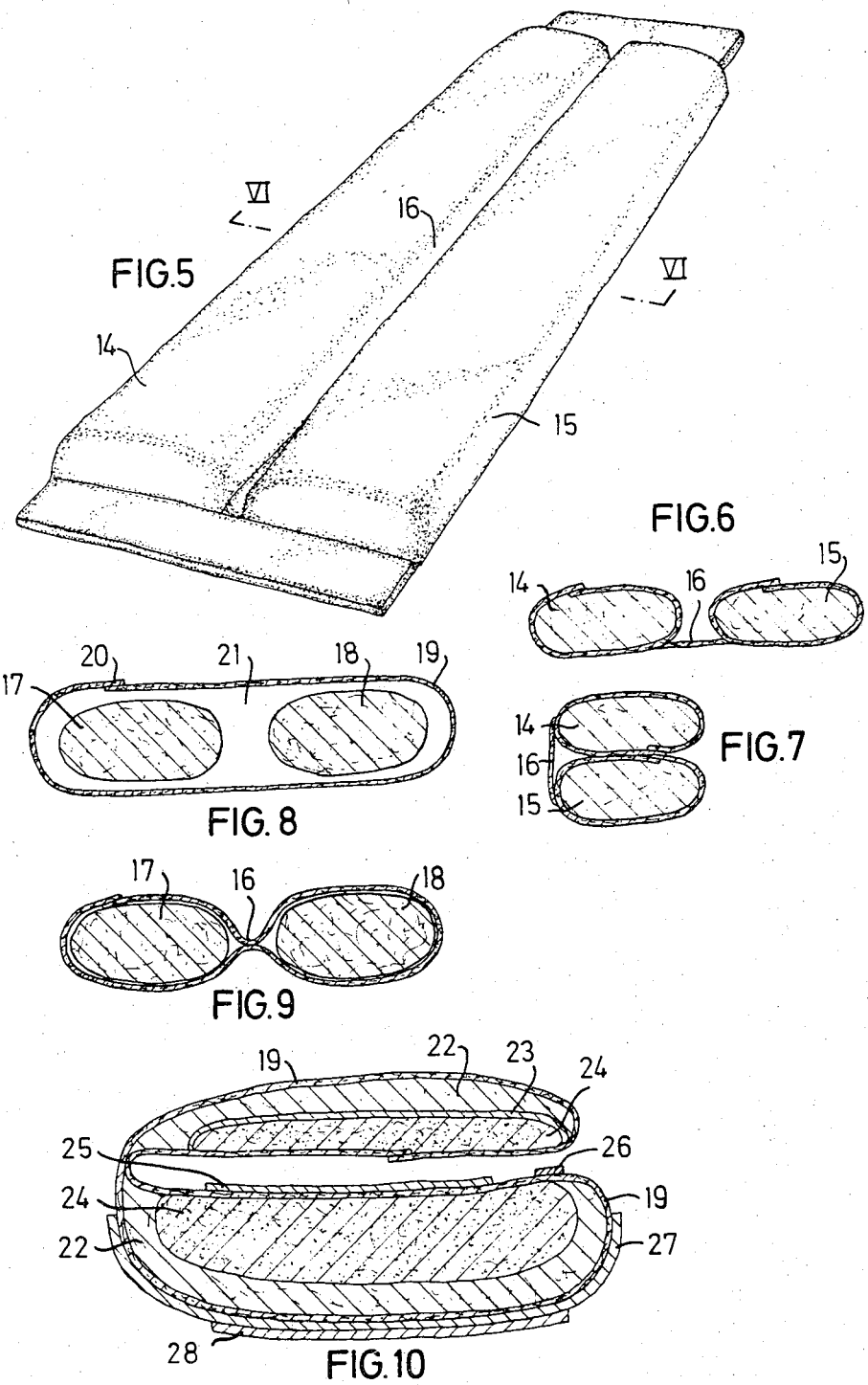

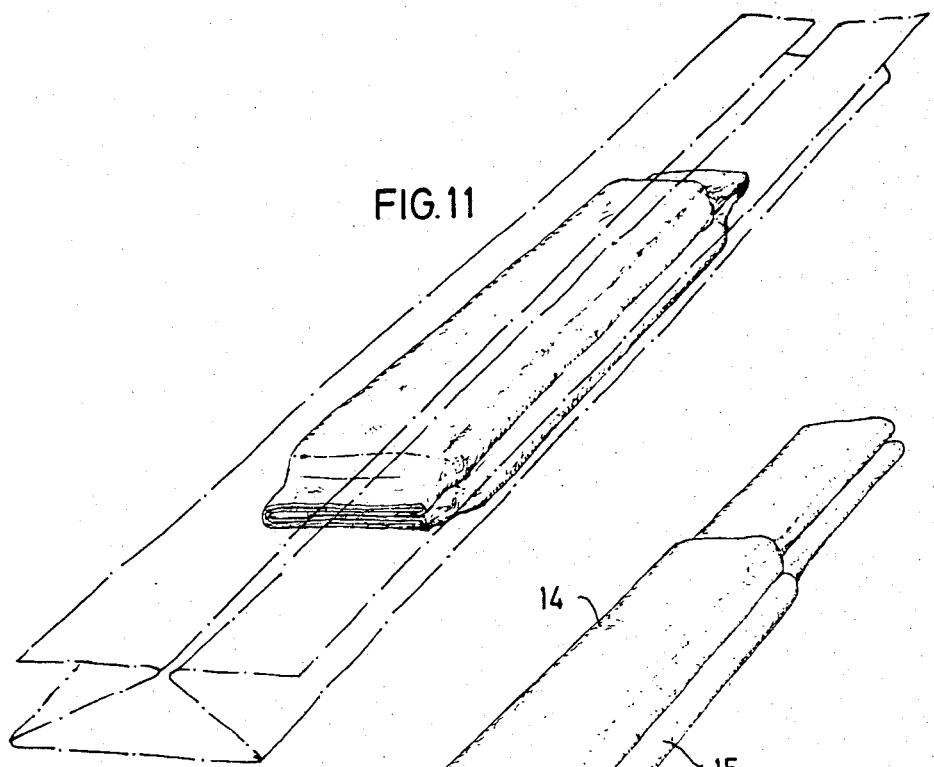
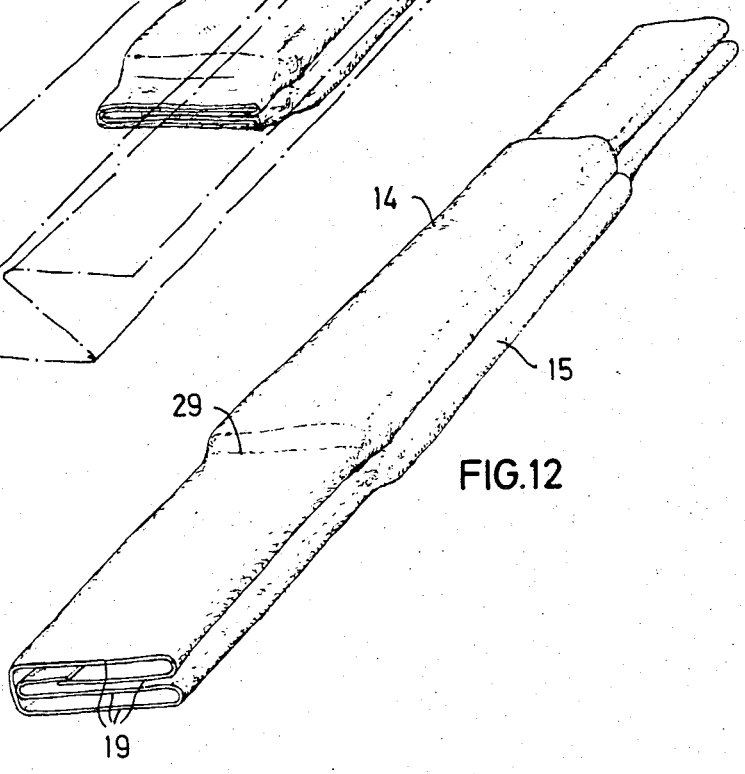

DEODORIZING AND DISINFECTING LIQUID-ABSORBING PRODUCT AND PROCESS FOR PRODUCTION THEREOF

The present invention relates to liquid-absorbing, deodorizing and disinfecting products such as sanitary napkins, surgical dressings, compresses, bandages, diapers or the like. The invention also relates to a process for production of such products.

During menstruation, or when there are discharges after childbirth or urinary incontinence, sanitary napkins are used to collect the fluid given off. There are napkins on the market with a suction effect, but none which prevent bad odor occurring at the same time. An additional problem in this connection is caused by fungal or bacterial infections which can thrive between the skin and the napkin. Similar problems with unpleasant odor and infections also arise under bandages, compresses and the like.

Attempts have been made to overcome problems with infections and odor in sanitary napkins by making the napkins in several layers with an easily permeable hydrophobic layer on top and an absorbent spreading layer thereunder, followed by a liquid-impermeable layer. This reduces to a certain extent the irritation to the skin and mucous membranes, but the problem of odor formation in the collected blood and urine remains.

A further attempt to overcome the odor problem is described in U.S. Pat. No. 3,804,094, according to which periodic acid was shown to be effective when impregnating the layer of the napkin which touches the skin. When the fluid penetrates, the periodic acid functions as an oxidation agent and prevents in this manner the occurrence of offensive odor. The effect of the impregnation agent on the mucous membranes remains a problem, however. That such an effect occurs is evident from the examples in said patent, which state that a deodorizing effect remains 5-8 hours after the sanitary napkin has been removed.

According to the abovementioned patent, tests have been made with peroxides as impregnating agents. These have, however, been shown to have insufficient effect and furthermore irritate the vagina and destroy its bacteria flora.

The purpose of the present invention is to achieve a sanitary napkin, a surgical dressing, a compress, a bandage or the like which effectively prevents the creation of unpleasant odor without irritating effect on the skin or mucous membranes. Another purpose is to prevent the growth of bacteria or fungi in such a product and to achieve disinfection of the collected blood, urine, wound fluid or the like.

According to the present invention it is now surprisingly possible to overcome the problem of skin and mucous membrane irritation and at the same time obtain a good deodorizing and disinfecting effect by arranging an area of a substance which gives off oxygen when in contact with moisture inside a napkin or compress at a distance from the surface which is to be placed against the body. The oxygen producing substance will thus not come into contact with skin or mucous membranes, thus overcoming the irritation problem. In contrast to the findings according to the U.S. Pat. No. 3,804,094, it was found that oxygen producing compounds such as organic peroxides, percarbonates, perborates and persulphates are effectively deodorizing, even when placed in a layer inside the napkin or compress. Especially effective are aryl peroxides, alkyl-peroxides and alkyl-aryl peroxides.

The present invention thus relates to a deodorizing and disinfecting fluid absorbing product, such as a napkin, compress, bandage, surgical dressing or the like, which can be made in one or several layers and is intended for absorption of a fluid such as menstrual fluid, blood, urine, wound fluid, perspiration or the like. The product is characterized in that it contains, in an inner area or layer, a substance which when supplied with moisture gives off active oxygen.

Compounds which give off oxygen in moisture are well known within the field and can, for example, be peroxides, ozonides, superoxides, oxo-ozonides and addition compounds between inorganic and organic compounds and peroxides. Examples of usable compounds are lithium peroxide, $Li_2O_2$, sodiumperoxide $Na_2O_2$, potassiumperoxide $K_2O_2$, rubidium peroxide $Rb_2O_2$, cesium peroxide $Cs_2O_2$, ammonium peroxide $(NH_4)_2O_2$, calcium peroxide $CaO_2$, strontium peroxide $SrO_2$, barium peroxide $BaO_2$, magnesium peroxide $MgO_2$, calcium peroxide $CdO_2$, mercury peroxide $HgO_2$, lithium superoxide, $LiO_2$, sodium superoxide $NaO_2$, potassium superoxide $KO_2$, rubidium superoxide $RbO_2$, cesium superoxide $CsO_2$, calcium superoxide $Ca(O_2)_2$, strontium superoxide $Sr(O_2)_2$, barium superoxide $Ba(O_2)_2$, lithium ozonide $LiO_3$, sodium ozonide $NaO_3$, potassium ozonide $KO_3$, rubidium ozonide $RbO_3$, cesium ozonide $CsO_3$, ammonium ozonide $NH_4O_3$, tetramethyl ammonium ozonide $(CH_3)_4NO_3$, hydrogen peroxide $H_2O_2$, potassium persulphate $K_2S_2O_8$, ammonium persulphate $(NH_4)_2S_2O_8$, silver peroxide $Ag_2O_2$, zirconiumperoxide $ZrO_3$, hafnium peroxide $HfO_3$, titanium peroxide $TiO_3$, phosphorus peroxide $P_2O_6$, sulphur peroxide $SO_4$, $S_2O_7$, rhenium peroxide $Re_2O_8$, ironperoxide $Fe_2O_6$, cobalt peroxide $CoO_2$, nickel peroxide $NiO_2$, sodium persulfate $Na_2S_2O_8$, sodium percarbonate $Na_2CO_4$, $Na_2C_2O_6$, potassium percarbonate $K_2C_2O_6$, potassium perphosphate $K_4P_2O_8$, ammonium perphosphate $(NH_4)_4P_2O_8$, barium perphosphate $Ba_2P_2O_8$, zinc perphosphate $Zn_2P_2O_8$, silver perphosphate $Ag_4P_2O_8$, potassium perborate $KBO_3$, ammonium perborate $NA_4BO_3$, sodiumperborate $NaBO_3$, dibenzoyl peroxide, di-4-methylbenzoyl peroxide, o-methyl benzoyl-peroxide, p-methoxy-benzoyl peroxide, acetyl benzoyl peroxide, benzoyl stearoyl peroxide, di-4-phenylbenzoyl peroxide, di-t-butylperoxide, diethyl peroxide, diacetyl peroxide, dicumyl peroxide, diheptanoyl peroxide, dekanoyl peroxide, lauroyl peroxide, diheptanoyl peroxide, distearoyl peroxide, disuccinyl peroxide, 3,5,5-trimethylhexanoyl peroxide, di(1-naphtyl) peroxide, tert-butyl perbenzoate, O,O-t-butyl-O-isopropyl mono-peroxycarbonate, stearyl percarbonate, 2-ethylhexyl percarbonate and sec-butyl percarbonate and corresponding perborates and persulphates.

The invention is not limited to the use of the above given substances.

The compounds which give off oxygen can furthermore be buffered to obtain a pH value which is suitable to the skin or mucous membrane and which facilitates the absorbtion of odorous substances such as ammonia and amines. For this purpose phosphates can be suitable.

Catalysts can also be required and in certain cases a retardant or stabilizer. For many of the compounds mentioned, iron is a catalyst, which accelerates the decomposition and thus the production of oxygen. In a product containing such a catalyst, haemoglobin iron can sometimes be sufficient as a catalyst.

When calculating the amount of the oxygen producing substance and of possible retarders and catalysts, the temperature at which the product shall be used must be considered and also the desired time that the effect must remain.

The oxygen producing products of the invention have the following advantages: they retard viral, bacterial and fungal growth, they are deodorizing and mildly cooling. The deodorizing effect is of great importance during menstruation and for urinary incontinence. The fungicidal and germicidal effect can also be exploited for example in the treatment of bedsore patients. Such patients have been treated previously with oxygen gas, by supply of the gas through the actual bed bottom. The use of a compress which gives off oxygen gas when moistened with wound fluid can have appreciable advantages.

It is also possible to arrange an oxygen producing layer within the compress in an adhesive bandage. This prevents the growth of anaerobic bacteria and breaks down the bacteria in the wound fluid. A further use possibility is in combination with an absorbent wound powder such as DEBRISAN ®. Such a powder helps keep a wound dry by soaking up wound fluid and blood. It does not provide any germicidal effect, however. By using a compress or a bandage with an interior layer, which gives off oxygen in moisture, on top of the wound powder, the double advantage is achieved that the powder is more easily kept on the wound and that the wound surface is disinfected. Another possibility is to incorporate in a bandage or a compress both a wound powder and an oxygen producing substance. In this way, the wound is kept dry and at the same time bacteria-free.

The present oxygen emitting layer can also be arranged in a shoe insole insert, either with or without a moisture absorbing substance. A similar construction can also be used for a perspiration pad or compress.

The following is a listing of some usable compounds with information on the catalysts and storage stability.

Urea peroxide $(NH_2)_2CO.H_2O_2$:

Ammonia and other alkaline substances catalyze the breakdown. Heavy metals and especially a combination of iron and copper ions gives a strongly catalytic effect. Also chelate complexes of copper, cobalt, manganese and iron can be used. The storage stability of pure urea peroxide is rather low but by using various additives (for example o-phthalic acid, 8-hydroxy quinoline) it is easy to stabilize the compound for storage at room temperature.

Sodium perborate $NaBO_2.H_2O_2.4H_2O$, $NaBO_2.H_2O_2.3H_2O$ and $NaBo_2.H_2O_2$:

Metal silicate compounds and metal phosphate compounds are well suited as catalysts. Combinations of metals can be used, for example the metals copper, cobalt, manganese and iron. The storage stability is good. Said compounds contain 8.9, 10 and 15.5% active oxygen respectively.

Hydrogen peroxide $H_2O_2$:

Catalysts are combinations of copper clartrate compounds and iron salts. Even salts and oxides of the metals lead, mercury, silver, cobalt, nickel and manganese can be used. These have catalyzing action in all pH ranges. In alkaline environment, copper citrate complexes are good catalysts. The storage stability for pure hydrogen peroxide is low. The percentage of active oxygen is 10% in 35-percent hydrogen peroxide.

Sodium chlorate $NaClO_3$ and sodium perchlorate $NaClO_4$:

Finely distributed metals catalyze the decomposition. The storage stability is good. Heating is required to make the oxygen leave. 15% active oxygen in $NaClO_3$ and 13% in $NaClO_4$.

Sodium percarbonate $Na_2CO_3.1,5\ H_2O_2$:

Copper citrate complexes are excellent catalysts. Magnesium silicate functions as a stabilizer. (Pure percarbonate $Na_2CO_4$ has a lower stability than the carbonate perhydrate.) 10.4% active oxygen.

Sodium peroxide $Na_2O_2$:

Catalysts are iron oxide, manganese oxide, vanadium oxide, chromium oxide, cobalt oxide, nickel oxide, oxides of rare earth metals. Carbon dioxide and water produces with sodium peroxide oxygen. The storage stability is good in dry atmosphere. 20% active oxygen. It can be necessary to use retardants.

Organic peroxides, for example

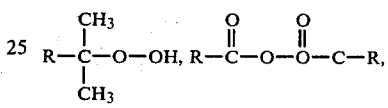

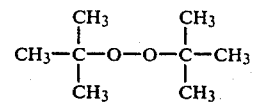

The storage stability is low. The oxygen gas content is often very low since the major portion of the molecule consists of a bulky organic component. Di-t-butyl peroxide has good stability. Suitable organic peroxides are alkyl and aryl peroxides and organic persulphates, percarbonates and perborates.

Persulphates, e.g. $K_2S_2O_8(NH_4)_2S_2O_8$:

Sulphuric acid and heating facilitates breakdown. High stability. Rather low content of active oxygen. When broken down forms essentially hydrogen sulphate, but there is some risk for the formation of sulfuric acid. The acidic solution formed should be able to absorb occurring ammonia and volatile amines.

Potassium superoxide $KO_2$:

Water and carbon dioxide in reaction with potassium superoxide produce oxygen. Good storage stability in dry atmosphere. High percentages of oxygen. The decomposition rate of the compound in water is high, so retarding substances may be necessary.

Other peroxides and substances giving off oxygen gas

| Other peroxides and substances giving off oxygen gas | | |
|---|---|---|
| Oxygen producing substance | Formula | Remarks |
| Silver peroxide | $Ag_2O_2$ | Expensive |
| Ozonides | $KO_3, NaO_3$ | Too reactive, risk for explosion |
| Oxo-ozonides | $R_4C_2O_4$ | Unsaturate comp. + ozon. Unstable. |
| Perphosphate | $K_4P_2O_8$ | Stable, can possibly be used |
| Potassium permanganate | $KMnO_4$ | Colors too much |
| Phosphate perhydrate | $Na_2HPO_4.H_2O_2$ | Fairly stable can poss. be used |
| Cosalene | | A cobalt-containing |

| Other peroxides and substances giving off oxygen gas | | |
|---|---|---|
| Oxygen producing substance | Formula | Remarks |
| | | substance. |

Of the listed compounds the following have proved especially useful: Inorganic and organic persulphates, percarbonates and perborates, preferably the organic compounds alkyl, aryl and alkylaryl peroxides with 1–25 carbon atoms in the alkyl groups, preferably 1–20 and especially 1–10 carbon atoms.

The following two peroxides appeared to be more suitable than others:

1. Sodium perborate (or borax peroxide). Advantages: inexpensive, costs ⅓ as much as urea peroxide; stable when stored; well known preparation; high pH and therefore non-irritating to the skin. Disadvantages: the high pH value prevents ammonia and amines from being easily absorbed by the moistened substance.

2. Urea peroxide. Advantages:

well-known preparation; no insoluble residues are built in the reaction; low pH (2.8) enables ammonia and volatile amines to be easily absorbed; good disinfectant ability; non-irritating to the skin. Disadvantages: high cost, low pH value can irritate wounds when used for long periods.

The substance which gives off oxygen in moisture can be incorporated in the present product as a powder or by impregnation of an absorbent layer with a solution of the substance. It is also possible to use microcapsules to enclose the substance. In this case, the substance does not need to be enclosed in plastic or the like during storage to prevent initiation of the production of oxygen gas during storage. Before use, one can rub the product between one hands or press it together between ones fingers (for example in a sanitary napkin or a bandage) to expose the oxygen producing substance. When using the oxygen producing substances in microcapsule form, for example in an insole, the capsules are automatically crushed when used, so that the oxygen producing substance can react with the moisture supplied. The construction with microcapsules should be especially advantageous when used in an insole or in an adhesive plaster or small compress, where the capsules can be easily crushed by pressing the product between ones fingers or hands before removing it from its envelope.

The product of the invention consists of a body of absorbing material, e.g. cotton, regenerated cellulose, synthetic fibers or synthetic cotton or foam rubber or cellular plastic. Inside the absorbent body there is a layer of a substance which gives off oxygen in moisture. There can be additional layers in the body, such as a spreading layer and an impermeable layer. As was mentioned above, the product, especially when used as an adhesive plaster or bandage, compress or insole insert, can also contain a highly absorbent powder. Either the powder layer can be arranged so that the penetrating fluid first comes into contact with the powder and then into contact with the oxygen producing substance, or vice versa, or that powder and the oxygen producing substance can be mixed with one another in one layer. It should be especially advantageous to arrange the layers so that the oxygen producing substance first becomes moist and the absorbent powder first then comes into contact with the fluid.

In selecting suitable materials for the body of the substance, one must take into account the decomposing effect of the active oxygen on the material so that no dangerous decomposition products are formed. Cellulose materials have shown themselves to be especially suitable, e.g. cotton-wool.

When producing the product according to the invention some problems may occur. In manufacture on a large scale the price of napkins and diapers might increase considerably if they were packed as moisture proof as required to prevent inactivation during storage in moist air of the substance which gives off oxygen in moisture.

Further problems are the humidity in factories manufacturing the liquid-absorbing products, dust formed by the substances which give off oxygen in moisture, which in combination with cotton dust can create a danger of explosion and fire. A further problem is that it can be necessary to produce many different diapers and sanitary napkins with different dosages of the deodorizing substance. Increasing the freedom of choice in this manner would involve large price increases.

The further purpose of the present invention is thus to achieve the liquid-absorbing deodorizing product of the invention without the abovementioned disadvantages.

For this purpose, the invention is directed to a liquid-absorbing product which is divided in two parts in such a manner that an insert or filler, such as medicine or a substance giving off oxygen in moisture, in the form of a strip or a powder, can be incorporated between the parts, one part being laid on top of the other to form the finished product.

The present invention thus also relates to a liquid-absorbing product, such as a sanitary napkin, a diaper, a diaper inlay, a compress, a bandage or the like, which is designed to be able to be provided with an insert such as a deodorizing strip or powder which gives off oxygen gas in moisture, said product having essentially the form of a rectangular or square pad comprising one or more layers of absorbent material, a thin jacket around this material, and possibly an anti-slip layer and/or an impermeable layer along a portion of the surface of the product. The product is characterized in that it is divided into two essentially identical, essentially rectangular or square parts of a thickness less than that of the product, which are joined along one side of each part by a thin flexible joint in such a manner that the parts can be placed on top of one another by folding the joint and then forming the entire product in the form it is to be used.

The joint is suitably made of the same material as the jacket, whereby the joint can be especially an integrated part of the jacket. The product can be made up of two thin pads lying side by side, with two sides parallel and with a gap between them. The two pads, several layers of liquid-absorbing material for example, possibly with a thin, easily permeable, non-absorbing layer around this material, lie in a sleeve of jacket material, which sleeve can be pressed together in the gap between the pads and fused or glued to form the joint. The ends of the sleeve which lie somewhat outside the ends of the two pads, can be fused or tied. If the ends of the sleeve are tied, it is suitable to first lay the pads on top of one another by folding the joint and then tying the sleeve. The knot will thus be opposite the middle line of the end side of the finished product thus holding the parts together to a certain extent when folded at the same time as it is easy midway between the ends to separate the parts sufficiently to insert a deodorizing strip for example. The parts can also be held together by folding the joint so that one part lies on top of the other, and pressing together the four layers of sleeve material which stick outside the ends of the pads, in the plane for the intermediate surface between the pads and joining them closely adjacent to the ends of the pads. Also in this case it is possible to separate the parts from each other enough for inserting a deodorizing strip.

To further prevent slipping of the parts against each other when using the product, it can be suitable to attach a strip or a layer of anti-slip material, e.g. foamed plastic, along the surface of one or both parts which are to face each other. If the entire surface of one part is covered with an anti-slip layer, this layer must be permeable to liquid, for example, be made of foamed plastic with open pores. It can, however, be suitable to arrange a narrow strip or a piece of a strip on only a portion of the inner surface of the part, suitably near the edge of the surface which does not lie close to the joint. In this case also the anti-slip strip can suitably be easily permeable.

The present invention also relates to a simple process for the manufacture of the described product.

In the process according to the invention, two thin, essentially square or rectangular pads are made, which together make up the layers which are to be inside the jacket in the finished product. The pads are laid side by side, with two sides parallel and with a gap between them on a web of sleeve material in such a manner that the gap is parallel to the length of the web. The width of the web should be somewhat larger than the circumference around the pads lying side by side. The web is then folded lengthwise tightly around the outer edges of the pads and the edges of the web are joined together on top of one pad so that the pads will lie enclosed by a sleeve of the web with a seam parallel to the gap. The sleeve is then cut off on either side of the pads. Alternatively, the web can be cut first and then the sleeve be formed by folding and joining the sleeve around the pads.

Between the pads in the gap there will be two layers of jacket material. These two layers form together the joint between the pads. The layers can also be joined by glueing or fusing in the gap. Outside the ends of the pads, the sleeve can be flattened and a seam be formed in the plane of the pads. The seam along the ends of the pads and the seam in the gap between the pads can also be formed before the sleeve is cut off. It is also possible to first fold the joint and place one pad on top of the other and then make a seam of four layers of jacket material on either side of the product or to tie together the material lying outside the pads into a knot on either side of the product. An impermeable layer and possibly also an anti-slip layer can be fastened to an outer surface of the product formed. An anti-slip layer or strip can also be attached to an inner surface of one of the pads after making the sleeve.

It is quite simple to adapt an existing production line for diapers, sanitary napkins, compresses and the like to the production of the present products, since the same materials are used as previously. Instead of forming one pad of absorbent material on a web of jacket material, two pads are formed with a combined thickness equal to that of the entire product, said pads lying side by side on a web of jacket material which is approximately twice as wide as the conventional web. The rest of the steps in the process are similar to the conventional steps.

With the present new two part product of the invention it is thus easy to achieve the deodorizing product of the invention, which is provided with a deodorizing insert or medicinal filler. The deodorizing insert is stored and manufactured separately. This eliminates the need for having dry air in factories for diapers and sanitary napkins. Furthermore, the liquid-absorbing two part product can be packed and stored in a conventional manner without the need for air-tight and moisture-proof packagings. The fire hazard, which can arise through a direct combination of large amounts of cotton material and oxidizing material in a single package, is also eliminated.

The absorbent two part product of the invention can be used without any insert material, with only a small amount of insert material, e.g. a piece of a deodorizing strip, or with a large amount of insert material, e.g. several pieces of a deodorizing strip. The two part product may also be used with other inserts than a deodorizing one.

The deodorizing substance which gives off oxygen in contact with moisture can be inserted into the two part product in the form of a strip, a powder or possibly a paste. For example, a strip of an absorbent material, such as cloth, can be impregnated with the substance which gives off oxygen in moisture. The strip can then be wound into a roll and placed in a moisture-proof container, from which a piece at a time can be taken and clipped off. The entire strip can also be enclosed in a moisture-proof jacket, e.g. plastic. The strip can possibly be provided with perforations for easy separation of suitable lengths of the strip. Such an impregnated strip can also be combined with an anti-slip strip, such as a strip of foamed plastic with open pores. It may also be possible to use the strip of foamed plastic itself as a carrier for the substance which gives off oxygen in moisture. By combining the oxygen producing substance and anti-slip strip in one, e.g. a two layer strip, the use of an anti-slip strip on the inside of one part in the liquid absorbing product can be avoided.

The material which gives off oxygen in moisture can also be inserted enclosed in microcapsules. The capsules can be used in loose form and be spread out in the liquid absorbing product between the parts or they can be stuck to a strip which is inserted into the product. When the product is to be used, the oxygen producing material can be easily activated by pressing the capsules together so that they are crushed.

The invention will be described in more detail in the following, in which, for the sake of simplicity, we will only refer to a sanitary napkin, a diaper and a wound compress. The construction of compresses and the like in different layers is similar to the construction of a sanitary napkin and the invention is thus not intended to be limited to the embodiments described below.

Several embodiments of the invention are described with reference to the accompanying drawings, in which FIG. 1 shows a schematic perspective view of a deodorizing sanitary napkin according to the invention, sectioned at one end, FIG. 2 shows a section through the napkin in FIG. 1, FIG. 3 shows a section through another embodiment of a napkin according to the invention, FIG. 4 shows a section through a wound with wound powder and compress lying on top of it, FIG. 5 is a schematic perspective view of a two part product according to the invention, FIG. 6 shows a section through the plane VI—VI in FIG. 5, FIG. 7 shows the same product as in FIG. 3 with the two parts of the product lying on top of one another.

FIGS. 8 and 9 show a section similar to FIG. 6 through another embodiment of the invention.

FIG. 10 shows a detailed section through a preferred embodiment of a sanitary napkin or diaper according to the invention.

FIG. 11 shows a perspective view of a two part diaper inlay according to the invention inside a diaper and FIG. 12 shows a perspective view of a two part napkin or diaper according to the invention during a production step.

Figure 1:
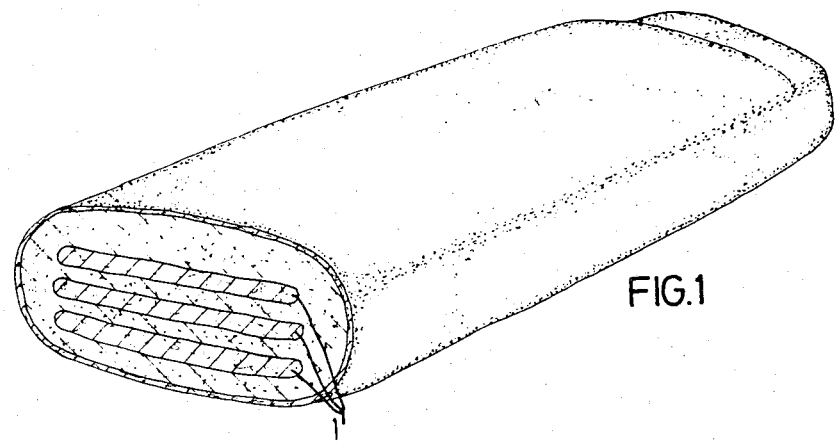
Figure 2:
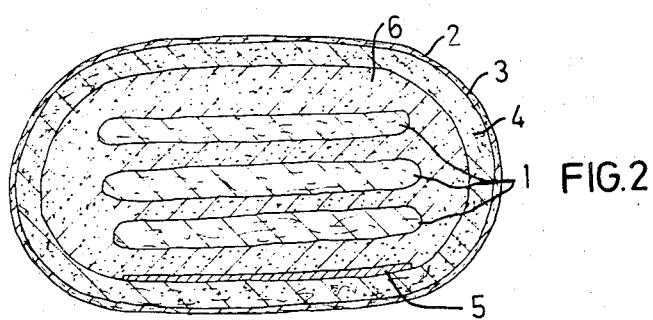
Figure 3:
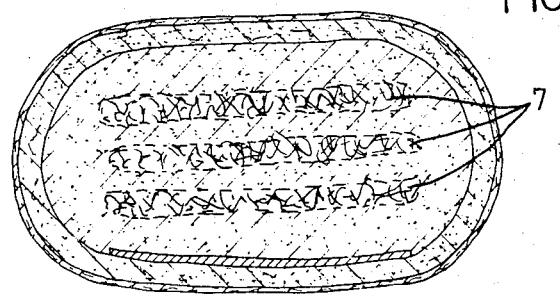

The sanitary napkins shown in FIGS. 1, 2 and 3 are of conventional construction and consist of a hydrophobic, easily permeable surface layer 3, a cotton layer 4, an absorbent body 6, which can contain a special spreading layer, and a sealing plastic layer 5, which delimits the lower portion of the absorbent layer. During storage, this napkin can also be enclosed in a separate envelope, e.g. a plastic film 2. Several layers 1 of an oxygen producing substance are arranged in the absorbent body in the sanitary napkin shown in FIGS. 1 and 2. The oxygen producing substance can be provided as a powder or by impregnation in a porous material, e.g. foamed plastic, or can be enclosed in a porous bag. The material or bag can be cut into suitable lengths and widths and be laid as strips in the absorbent portion of the sanitary napkin. That portion of the napkin which during use will lie closest to the skin or mucous membrane, thus does not contain any oxygen producing substance. Rather, the first strip 1 is farther into the napkin. Production is facilitated by using pre-made strips, which are then laid in the napkin. In the embodiment in FIG. 3 the oxygen producing 7 substance is not inserted in the form of strips but is layered directly with the absorbtion material 6. It is also possible to produce a sanitary napkin by preparing the absorbent material in layers with a compound which gives off oxygen in moisture, whereby the oxygen producing substance will consist of for example sodium percarbonate and cellulose which is laid as a strip into the napkin's absorbent material 6, e.g. cellulose.

When using the napkin the envelope 2 is removed. When moisture, e.g. menstrual fluid or urine, penetrates into the napkin, the oxygen-producing substance is broken down and gives off active oxygen, which decomposes bacteria, fungi and odorous substances. The plastic layer 5, which lies in the portion of the napkin which is away from the body, gives rise to an oxygen development which is directed towards the body. The use of such a plastic layer is especially important when a directed oxygen effect is desired. The napkins can also be made so that certain of them contain larger amounts of active material and can thus give off more native oxygen. These napkins can be used during the first days of menstruation. Napkins with a smaller amount of active material can be used thereafter.

Figure 4:
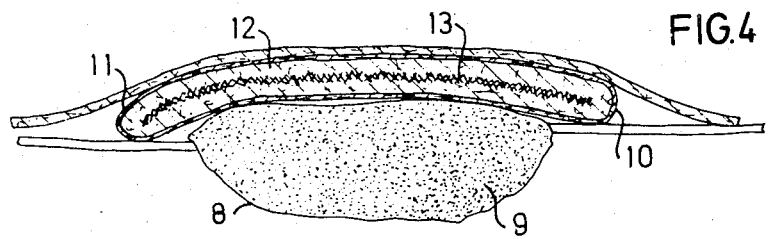

FIG. 4 shows a wound on an arm for example. The wound surface 8 is covered with a powder 9, which absorbs the wound fluid. The powder can be held in place by a compress 10 consisting of an outer protective cover 11 and thereunder a layer of cotton 12 and inside this layer a layer of substance 13 which gives off oxygen in moisture. When the wound discharges fluid it is sucked up by the wound powder 9 and by the layer of cotton 12. Oxygen is then produced in the oxygen producing layer 13, thereby keeping the wound dry, disinfected and aired.

FIGS. 5–9 show schematically a two part product according to the invention. The product consists of two parts 14 and 15 with a thin joint 16 between them. Via the joint, the product can be folded and one part 14 be laid on top of the other 15, as shown in FIG. 7. An insert such as a salve or a deodorizing strip, can be easily inserted between the parts. FIGS. 6 and 7 show how the joint can be formed by fastening a strip, of the jacket material for example, between two finished parts. FIGS. 8 and 9 show another possibility. In this embodiment two pads 17 and 18 are first formed of the layers which are to be inside the jacket 19 in each part. These pads 17,18 are placed with two sides parallel and with a gap 21 between them on a strip or web of jacket material 19. This strip or web is then folded around the pads and the edges of the strip or web are joined into a seam 20 so that the pads lie inside a sleeve. Then the two jacket layers in the gap 21 are pressed together and are glued together, thus forming the joint 16. Even without being glued together, the two jacket layers in the gap can function as a joint.

FIG. 10 shows in detail a section through a preferred embodiment of a two part product produced in the manner described in connection with FIGS. 8 and 9. The product consists of two parts 14 and 15 with a joint 16 therebetween, said joint being formed by two layers of the jacket 19 between the two parts. The upper part is thinner than the lower part. The top side of the upper part is intended to lie against the body of the user. The upper part consists, as seen from the top and down, of a layer of jacket material 19, a layer of easily permeable, nonabsorbent material 22, e.g. wool of hydrophobic fibers, a spreading layer 23 and a thin layer of highly absorbent material 24. Below this there is an additional layer of the jacket 19. The spreading layer can possibly be made as a sleeve around the highly absorbent material 24. The lower portion of this sleeve would lie directly against the lower portion of the jacket. It is possible to eliminate the layer 24 from the upper part.

The lower thicker part consists as viewed from the top down, of a jacket layer 19, a thick layer of highly absorbent material 24, a thin layer of non-absorbing material 22, a jacket layer 19, a moisture-proof layer 27 and an anti-slip layer 28. The layers 27 and 28 can be made as one in the form of a foamed plastic layer for example, which has a non-porous plastic film on one side.

A strip 25 of a substance which gives off oxygen in moisture can be placed on top of the lower part. This strip can be laminated with an easily permeable foamed plastic strip, so that the slipping effect between the upper and lower parts is prevented when the strip is inserted between the parts. The lower or upper part can also encompass, on the surface facing the other part, a layer or a strip 26 of anti-slip material. This strip or layer can also be inserted as a separate insert.

When the two part product in FIG. 10, for example a diaper, sanitary napkin, or compress, is used, the liquid discharged from the user, e.g. wound fluid, urine, or blood, passes rapidly through the jacket 19 and the non-absorbent layer 22 without being spread. In underlying the spreading layer 23, the liquid is spread out over its entire surface and is then absorbed in the thin absorbing layer 24 and moistens through the jacket 19 lying thereunder. The insert 25 thus becomes moist and begins to give off oxygen, which penetrates up into the absorbent layer 24 deodorizing it, and down into the underlying thicker layer 24 at the same time as the liquid is spread in this layer. Deodorizing is also achieved in this layer. The liquid is prevented from escaping from the lower part by the non-absorbing layer 22 and the tight layer 27. If the product is a sanitary napkin or a diaper, the product can be held in place with the aid of an anti-slip layer 28. It is also advantageous between these parts to insert a piece or a strip or a layer of anti-slip material so that the two parts are not displaced from one another during use.

The two part product of the invention can thus be used directly as a diaper, compress, sanitary napkin or bandage. There is, however, a folded diaper, a so-called "wing diaper," with the form shown with dashed lines in FIG. 11. Due to the folds, it can be somewhat awkward if this diaper is made in two parts. If deodorizing is desired when using such a diaper, it may be better to make a thin two part insert diaper in accordance with the present invention and insert this insert diaper between the layers of the wing diaper as shown in FIG. 11. A deodorizing strip can be placed between the parts of the insert diaper. Due to the insert diaper, the absorption capacity of the wing diaper can be increased at the same time as deodorizing is achieved.

The two part product of the invention is easily produced by folding a web of jacket material 19 around two pads 17,18 as shown in FIGS. 8 and 9 and joining the edges of the web into a seam 20 parallel with the gap 21 extending between the pads. The sleeve thus formed can then be cut off, either close to the ends of the pads, or at a distance therefrom. A seam can be made along the ends of the pads, as shown in FIG. 5. It is also possible to first fold together the joint 16 between the parts and thereafter join together the four layers of jacket material which will lie on either side of the pads lying on top of each other, e.g. along the line 29 as shown in FIG. 12. If the seam is formed along the line 29, the jacket is then cut along the seam. Instead of a seam, the jacket layers can be tied in two knots at a distance from the pads. The knots or seams will hold the two parts of the product together, but it is still easy to pull apart the parts in the middle of the product and insert a deodorizing strip, powder or a medicinal salve between the parts.

The two part product is most easily manufactured in the form of an essentially square or rectangular pad. The joint between the two parts is then easily made only so wide that one part can be laid on top of the other. It is, however, also possible to make a product with the form of an oval pad. The joint between the parts will then be wider near the ends of the product and when folded the wider portion can stick out somewhat outside the product. In certain uses this can cause irritation to the skin, for example when the product is a sanitary napkin or a diaper. In other uses, e.g. when the product is a compress or a bandage, the protruding portion of the joint is of no importance and the product can therefore have an oval shape.

The following examples illustrate the odor inhibiting effect of the present sanitary napkins and compresses.

EXAMPLE 1

A conventional sanitary napkin was prepared by cutting it apart straight through the absorbent layer, parallel to the direction of the layers. Crushed power of ASCOXAL ®-T, Astra Läkemedel AB, Sweden (ca. 1.5 tablet per napkin) was spread out on the cut surface. One tablet of ASCOXAL ®-T consists of 0.1 g ascorbic acid, 70 mg. sodium percarbonate (10% active oxygen) and 0.2 mg. anhydrous copper sulphate.

Three such prepared napkins and three unprepared napkins were used. Odorous urine was poured on the six napkins. In the three prepared napkins the urine odor disappeared almost immediately. In the three unprepared napkins the odor remained.

EXAMPLE 2

Napkins were prepared in the same manner as in the above example. These napkins were used by a woman during three menstrual periods. Overnight a single sanitary napkin was used for as long as 12 hours or more. At no time during this period was there an offensive odor. No discomfort was experienced.

It is clear from the above examples that the present sanitary napkins and compresses can be used without discomfort and with deodorizing effect.

EXAMPLE 3

The odor-inhibiting effect of urea peroxide was investigated in five trials.

TRIAL 1

In a test tube containing 0.4 g urea peroxide (urea/hydrogen peroxide 1:1) in solid form and without catalyst, 10 drops of 5% ammonia solution was added. Already after one minute the ammonia odor could no longer be detected. The tube was loosely closed with a Teflon plug during the trial. The volume in the tube was about 10 ml. Strong cooling effect upon the partial dissolving of the crystals after the addition of the ammonia.

TRIAL 2

The same conditions as in Trial 1, but with the addition of 10 drops 25% ammonia solution (i.e. so-called concentrated ammonia) + 10 drops water. All the urea peroxide dissolved. A heavy oxygen production was obtained immediately after the addition of the ammonia. After 1 minute there was still a strong ammonia odor. When shaking the tube the production of oxygen was temporarily increased (slight foaming). Without shaking, the solution acted like mildly effervescing soda water. Even after 4 hours the ammonia odor was still strong, so the conclusion was drawn that the dosage of ammonia was too large.

TRIAL 3

One drop of 25% $NH_3$ was placed in a test tube. A plug of a piece of fine glass-wool was placed on top of it, followed by a layer of urea peroxide and an additional piece of glass-wool. Five drops of water were dropped on the urea peroxide before the upper glass-wool plug was put in place. No ammonia odor could be detected after 2 hours.

TRIAL 4

The same conditions as in Trial 3, but with the addition of 5% catalyst to the urea peroxide. Heat production in the peroxide layer after a few minutes and heavy oxygen production. After two hours the peroxide layer was removed with a tweezers. No ammonia odor could be detected. (The catalyst was prepared as follows: 1 part $CuSO_4.5\ H_2O$ + 1 part $(NH_4)_2Fe(SO_4)_2.7\ H_2O$ was mixed and heated to 220° C. for thirty minutes. The mixture was ground and then used as a catalyst.)

TRIAL 5

The same conditions as in Trial 2, but with 2 drops of concentrated ammonia + 18 drops of water. No ammonia odor could be detected after 2 hours (That is, the odor could have disappeared earlier, but no smell test was performed earlier. This also applies to Trials 3 and 4).

EXAMPLE 4

The urea peroxide used was produced in the following manner.

6.23 g carbamide was heated with 0.19 g o-phthalic acid to 95° C. 5.14 g 71.1% hydrogen peroxide (=4.14 g 88% $H_2O_2$ + 1.00 g water) was added to the hot solution. The hydrogen peroxide solution was heated to 108.5° C. before the addition. The mixture was shaken, which produced a clear solution. After 3 minutes (the temperature had then dropped to 68° C.) the mixture was poured out onto a cold surface, and crystals immediately began to be precipitated. The crystals were dried for 10 days. The material was mortared in small amounts and was then transferred to a vessel which could be tightly sealed.

The products and process of the invention have been described with reference to preferred embodiments. Modifications of the invention will be obvious to those skilled in the art and the invention is only to be limited by the following claims.

What I claim is:

1. Liquid-absorbing product, which is designed to be able to be provided with an insert or filler of a material which gives off oxygen in moisture, said product having the form of an essentially rectangular or square pad and comprising one or more layers of absorbent material, and a thin jacket around this material, characterized in that the product is divided into two essentially identical, essentially rectangular or square parts of a thickness less than that of the product, which are joined along one side of each part by a thin flexible joint in such a manner that the parts can be placed on top of one another by folding the joint and then form the product in the form in which it is to be used, and the material which gives off oxygen in moisture is in direct contact with the absorbent material.

2. Product according to claim 1, characterized in that the joint is made of the same material as the jacket.

3. Product according to claim 2, characterized in that the joint is an integral part of the jacket, and the product, when the parts lie side-by-side with the joint stretched, being made up of two thin pads enclosed together by the jacket in the form of a sleeve, the joint being formed by two jacket layers between the pads, said layers possibly being joined together, as by fusing or gluing.

4. Product according to claim 1, characterized in that the two parts have different thicknesses and that the thinner part consists of a jacket and inside the jacket an easily permeable hydrophobic material along the outer surface of the product, one or more spreading layers and possibly a thin layer of absorbent material against the inner surface of the part, and that the thicker part consists of a jacket and inside the jacket a hydrophilic absorbing material, possibly a spreading layer, and a hydrophobic layer along the outer surface of the part and outside the jacekt, along the outer surface possibly an impermeable layer and/or an anti-slip layer.

5. Product according to claim 1, characterized in that one or both of the parts, on the surface which is to face the other part, is provided with an easily permeable anti-slip layer or strip.

6. Product according to claim 1, characterized in that the jacket extends in the direction of the joint outside the absorbent material.

7. Product according to claim 6, characterized in that the portion of the jacket which lies outside the absorbent material, is joined together by gluing or fusing into a seam perpendicular to the joint, the seam either being made with the parts lying side-by-side in the plane of the parts or with the parts laid together so that the seam formed will hold together the parts on top of each other.

8. Product according to claim 6, characterized in that the jacket extending outside the absorbent material is tied on either side of the absorbent material with the two parts laid on top of each other so that the knots will be opposite the middle line of the end side of the product.

9. Process for the manufacture of a liquid-absorbing product according to claim 1, in the form of an essentially rectangular or square pad, said product comprising a jacket and one or more layers of absorbent material laid on top of one another, the product being made up of two essentially identical essentially rectangular or square parts of less thickness than the product, said parts being joined along one side of each part by a thin flexible joint, whereby the parts can be placed on top of each other by folding the joint and then form the product in the form it is to be used, characterized in that two thin, essentially square or rectangular pads are formed, which consist of the layers which are to be inside the jacket in the finished product, that the pads are laid side-by-side with two sides parallel and with a gap between them on a web of jacket material in such a way that the gap is parallel to the longitudinal direction of the web, the width of the web being somewhat larger than the circumference around the pads lying side-by-side, that the web is folded lengthwise tightly around the outer edges of the pads and that the edges of the web are joined together on top of one pad so that the pads will lie enclosed by a sleeve of the web, that the web is cut off on either side of the pads, whereupon the four layers of jacket material which will then lie on top of each other outside of the pads are joined together into a flat seam along the intermediate surface between the pads or are tied together into knots.

10. Process according to claim 9, characterized in that after joining the jacket into a sleeve, a strip or a layer of anti-slip material is fastened to a surface of the jacket which is to face the inside of the product.

* * * * *